US011880134B2

(12) United States Patent
Aqad et al.

(10) Patent No.: US 11,880,134 B2
(45) Date of Patent: Jan. 23, 2024

(54) SALTS AND PHOTORESISTS COMPRISING SAME

(71) Applicant: Rohm and Haas Electronic Materials LLC, Marlborough, MA (US)

(72) Inventors: Emad Aqad, Marlborough, MA (US); James F. Cameron, Marlborough, MA (US); James W. Thackeray, Marlborough, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 16/204,839

(22) Filed: Nov. 29, 2018

(65) Prior Publication Data
US 2019/0163058 A1 May 30, 2019

Related U.S. Application Data

(60) Provisional application No. 62/593,227, filed on Nov. 30, 2017.

(51) Int. Cl.
| | | |
|---|---|---|
| G03F 7/004 | (2006.01) | |
| G03F 7/16 | (2006.01) | |
| G03F 7/20 | (2006.01) | |
| G03F 7/26 | (2006.01) | |
| G03F 7/039 | (2006.01) | |
| C07C 309/10 | (2006.01) | |
| C07C 309/19 | (2006.01) | |
| C07C 62/06 | (2006.01) | |
| C07C 309/12 | (2006.01) | |
| C07C 395/00 | (2006.01) | |
| C07D 517/00 | (2006.01) | |
| C07C 309/06 | (2006.01) | |
| C07C 309/16 | (2006.01) | |
| C07D 345/00 | (2006.01) | |

(52) U.S. Cl.
CPC ............ G03F 7/0045 (2013.01); C07C 62/06 (2013.01); C07C 309/06 (2013.01); C07C 309/10 (2013.01); C07C 309/12 (2013.01); C07C 309/16 (2013.01); C07C 309/19 (2013.01); C07C 395/00 (2013.01); C07D 345/00 (2013.01); C07D 517/00 (2013.01); G03F 7/0042 (2013.01); G03F 7/0046 (2013.01); G03F 7/0397 (2013.01); G03F 7/16 (2013.01); G03F 7/2004 (2013.01); G03F 7/26 (2013.01); C07C 2603/74 (2017.05)

(58) Field of Classification Search
CPC ... C07C 395/00; C07C 391/00; C07C 391/02; G03F 7/0045; C07D 345/00
See application file for complete search history.

(56) References Cited

U.S. PATENT DOCUMENTS

| | | | |
|---|---|---|---|
| 4,689,288 A | 8/1987 | Buiguez et al. | |
| 5,712,078 A | 1/1998 | Huang et al. | |
| 6,787,281 B2 | 9/2004 | Tao et al. | |
| 3,039,194 A1 | 10/2011 | Glodde | |
| 8,039,194 B2 * | 10/2011 | Glodde | C07C 25/18 430/270.1 |
| 8,652,712 B2 | 2/2014 | Glodde | |
| 9,348,220 B2 | 5/2016 | Aqad et al. | |
| 10,781,276 B2 | 9/2020 | Enomoto et al. | |
| 2004/0214103 A1 | 10/2004 | Araki et al. | |
| 2009/0202943 A1 | 8/2009 | Ohsawa et al. | |
| 2010/0248149 A1 | 9/2010 | Tsuchimura et al. | |
| 2011/0020749 A1 * | 1/2011 | Ichikawa | G03F 7/0392 560/126 |
| 2011/0269074 A1 * | 11/2011 | Aqad | G03F 7/0392 430/311 |
| 2012/0052440 A1 * | 3/2012 | Yoshida | G03F 7/0045 430/326 |
| 2014/0186767 A1 | 7/2014 | Thackeray et al. | |
| 2015/0021289 A1 | 1/2015 | Ober et al. | |
| 2015/0177613 A1 | 6/2015 | Jain et al. | |
| 2015/0323866 A1 * | 11/2015 | Namai | C08F 220/1818 526/309 |
| 2016/0202608 A1 * | 7/2016 | Namai | C08F 220/26 430/270.1 |
| 2018/0267406 A1 * | 9/2018 | Nagai | C07C 303/32 |
| 2018/0273664 A1 | 9/2018 | Enomoto et al. | |
| 2019/0202955 A1 | 7/2019 | Aqad et al. | |

FOREIGN PATENT DOCUMENTS

| | | | | |
|---|---|---|---|---|
| JP | 07146528 A | * | 6/1995 | |
| JP | 09244233 A | | 9/1997 | |
| JP | 2001255647 A | * | 9/2001 | ........... C07D 211/76 |
| JP | 2001255647 A | | 9/2001 | |
| JP | 2008163242 A | | 7/2008 | |
| JP | 2017207532 A | | 11/2017 | |
| JP | 2018199781 A | | 12/2018 | |
| TW | 574184 B | | 2/2004 | |

OTHER PUBLICATIONS

English translation of JP2001255647. (Year: 2001).*
English translation of JP07146528. (Year: 1995).*
Zhou et al., "Te Nuclear Magnetic Resonance Study and X-ray Crystal Structures of Organotelluronium Salts", 1994, Organometallics, 13, 1575-1581. (Year: 1994).*
Sato et al., "First Detection of 2,2'-diphenylylenediphenylsulfurane and -selenurane [10-M-4(C4), M=S, Se] by Low Temperature NMR Experiments and Isolation of the Tellurane", 1995, Tetrahedron Letters, vol. 36 No. 16, 2803-2806. (Year: 1995).*
Fukunaga, Mari et al., "Synthesis and Property of Tellurium-Containing Polymer for Extreme Ultraviolet Resist Material," Journal of Photopolymer Science and Technology, vol. 30, No. 1, pp. 103-107.
Kanda T. et al in J. Org. Chem. 1999, 64, 8161-8169.
W.H.H. Gunther in Journal of Organometallic Chemistry, 1974, 74, 79-84.

* cited by examiner

Primary Examiner — Chanceity N Robinson
Assistant Examiner — Anna Malloy
(74) Attorney, Agent, or Firm — CANTOR COLBURN LLP

(57) ABSTRACT

New Te-salt compounds, including photoactive tellurium compounds useful for Extreme Ultraviolet Lithography.

17 Claims, No Drawings

SALTS AND PHOTORESISTS COMPRISING SAME

CROSS-REFERENCE TO RELATED APPLICATION

This Application claims the benefit of U.S. Provisional Application 62/593,227 filed on Nov. 30, 2017, which is incorporated by reference herein in its entirety.

FIELD

The present invention relates to new salt compounds that comprise one or more Te atoms. In one preferred aspect, photoactive tellurium salt compounds are provided that are useful for extreme ultraviolet lithography.

BACKGROUND

Extreme ultraviolet lithography ("EUVL") is one of the leading technologies options to replace optical lithography for volume semiconductor manufacturing at feature sizes <20 nm. The extremely short wavelength (13.4 nm) is a key enabling factor for high resolution required at multiple technology generations. In addition, the overall system concept—scanning exposure, projection optics, mask format, and resist technology—is quite similar to that used for current optical technologies. Like previous lithography generations, EUVL consists of resist technology, exposure tool technology, and mask technology. The key challenges are EUV source power and throughput. Any improvement in EUV power source will directly impact the currently strict resist sensitivity specification. Indeed, a major issue in EUVL imaging is resist sensitivity, the lower the sensitivity, the greater the source power that is needed or the longer the exposure time that is required to fully expose the resist. The lower the power levels, the more noise affects the line edge roughness (LER) of the printed lines.

Various attempts have been made to alter the make-up of EUV photoresist compositions to improve performance of functional properties. Among other things, a variety of photoactive compounds have been reported. See U.S. Pat. Nos. 8,039,194 and 8,652,712. See also US20150021289; US20150177613; and Fukunaga et al., J. Photo Polymer Sci., 2017, 30(1), 103-3-107.

Electronic device manufacturers continually seek increased resolution of a patterned photoresist image. It would be desirable to have new photoresist compositions that could provide enhanced imaging capabilities, including new photoresist compositions useful for EUVL.

SUMMARY

We now provide new salts and photoresists that comprise such salts. In preferred aspects, the salts can function as an acid generator, including a photoacid generator, and can be particularly useful for extreme ultraviolet lithography applications.

More particularly, in a first aspect, the present salts comprise one or more tellurium atoms, typically one or two tellurium atoms, including compounds of the following Formula (I):

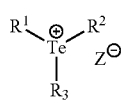
(I)

wherein $R^1$, $R^2$ and $R^3$ are each independently $C_{6-60}$ aryl group, a $C_{6-20}$ fluoroaryl group, a $C_{1-20}$ heteroaryl group, a $C_{7-20}$ aralkyl group, a $C_{7-20}$ fluoroaralkyl group, a $C_{2-20}$ heteroaralkyl group, or a $C_{2-20}$ fluoroheteroaralkyl group $C_{1-20}$ alkyl group, a $C_{1-20}$ fluoroalkyl group, a $C_{3-20}$ cycloalkyl group, a $C_{3-20}$ fluorocycloalkyl group, a $C_{2-20}$ alkenyl group, a $C_{2-20}$ fluoroalkenyl group, each of which is substituted or unsubstituted, $R^1$ is either separate or connected to the another group $R^2$ or $R^3$ via a single bond or a linking group to form a ring, and Z is an anion.

In certain preferred aspects, a tellurium salt (Te-salt) may comprise one or more optionally substituted phenyl substituents, such as salts of either the following Formulae (IIA) or (IIB):

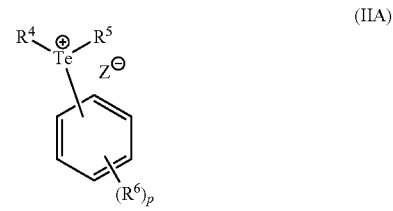
(IIA)

wherein in Formula (IIA):

$R^4$ and $R^5$ are each the same or different non-hydrogen substituent such as a $C_{1-10}$ alkyl group, a $C_{1-10}$ fluoroalkyl group, a $C_{3-10}$ cycloalkyl group, a $C_{3-10}$ fluorocycloalkyl group, a $C_{3-10}$ cycloalkoxy group, or a $C_{3-10}$ fluorocycloalkoxy group, each of which may be substituted or unsubstituted;

each $R^6$ is the same or different non-hydrogen substituent such as a halogen, —CN, —OH, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, or a $C_{3-10}$ fluorocycloalkoxy group, each of which except a halogen, —CN, and —OH may be substituted or unsubstituted;

p is an integer of 0 (where no $R^6$ groups are present) to 5; and

Z is a counter anion.

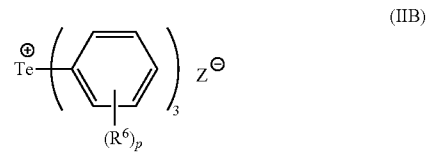
(IIB)

wherein in Formula (IIB):

each $R^6$ is independently a halogen, —CN, —OH, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, or a $C_{3-10}$ fluorocycloalkoxy group, each of which except a halogen, —CN, and —OH may be substituted or unsubstituted;

each p is the same or different integer of 0 (where no $R^6$ groups are present) to 5; and Z is a counter anion.

As discussed above, preferred Te-salts include those where a tellurium atom is a ring member, such as compounds of the following Formula (III):

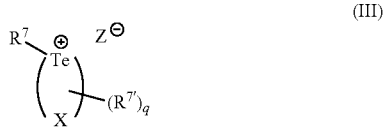 (III)

wherein:
X is a single bond or a connecting group such as S, O, C=O, S=O, SO2 and O—C=O (lactone); carbon, nitrogen, oxygen that together with the depicted Te atom forms a single ring group or a multiple fused or linked ring structure;
$R^7$ is a non-hydrogen substituent such as optionally substituted alkyl or optionally substituted carbocyclic aryl;
each $R^{7'}$ is the same or different non-hydrogen ring substituent such as halogen, —CN, —OH, such as optionally substituted alkyl, optionally substituted alkoxy or optionally substituted carbocyclic aryl;
q is an integer equal to 0 (where no $R^{7'}$ groups present) to the maximum valance permitted by the ring members; and
Z is a counter anion.

Particularly preferred Te-salts include fused ring compounds such as those of the following Formula (IIIA):

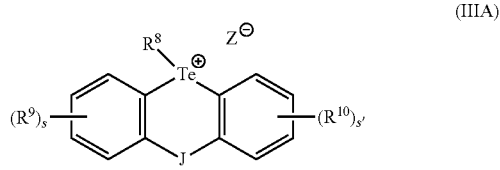 (IIIA)

wherein:
$R^8$ is a non-hydrogen substituent such as optionally substituted alkyl or optionally substituted carbocyclic aryl;
$R^9$ and $R^{10}$ are the same or different non-hydrogen ring substituent such as a halogen, —CN, —OH, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, or a $C_{3-10}$ fluorocycloalkoxy group, each of which except a halogen, —CN, and —OH may be substituted or unsubstituted;
J a single bond or a connecting group that suitably be selected from S, O, C=O, S=O, SO2 and O—C=O (lactone);
s and s' are each independently an integer of 0 (where no $R^9$ or $R^{10}$ substituents would be present), 1, 2, 3, and 4; and
Z is a counter anion.

In certain preferred embodiments, a Te-salt will comprise one or more acid-labile groups such as photoacid-labile ester or acetal groups.

In compounds of the invention (including a compound of any of the above Formulae (I), (IIA), (IIB), (III) and (MA)), the anion Z suitably can be an inorganic or organic group. Suitable inorganic groups include e.g. halogens such as I⁻, Br⁻, $sbF_6^-$, $BF_4^-$ and $B(C_6F_5)_4$. Suitable organic compounds may include aromatic and non-aromatic groups, including phenyl-containing anions and aliphatic anions such as $C_{1-30}$alkyl groups which may suitably contain one or more acid groups such as carboxylate, sulfonate, an anion of a sulfonamide or an anion of a sulfonamide and the like. Preferred organic anions have one or more electron withdrawing groups such as fluorine.

In certain preferred aspects, a Te-salt of the invention may be covalently linked to a polymer, for example one of either an anion or cation component of a Te-salt may be covalently linked to a polymer, or each of the anion and cation components of the Te-salt may be covalently linked to a polymer.

In certain preferred aspects, a Te-salt may comprise a polymerizable group such as an unsaturated group, for example a carbon-carbon unsaturated group, including activated vinyl groups such as an acrylate moiety. Such polymerizable groups can be reacted to covalently link an acid generator to other composition components such as a resist resin.

Preferred photoresists of the invention may comprise an imaging-effective amount of one or more Te-salts as disclosed herein and a suitable polymer component. The one or more salts suitably may function as an acid generator component in a photoresist composition. In this embodiment, a resist may comprise a mixture of distinct Te-salt compounds, typically a mixture of 2 or 3 different Te-salt compounds, more typically a mixture that consists of a total of 2 distinct Te-salt compounds.

Te-salts as disclosed herein also may be employed as a photodecomposable quencher (PDQ) such as in a photoresist composition together with another distinct acid generator that generates a stronger acid upon photoactivation that the Te-containing PDQ.

For use as a PDQ, a Te-salt may have an anion component having a relatively high pKa (e.g. sulfamate having pKa greater than 0 or carboxylate having pKa greater than 3). As referred to herein, pKa values are in aqueous solution at 23° C. and can be measured experimentally or calculated, for example using Advanced Chemistry Development (ACD) Labs Software Version 11.02.

Preferred Te-salts of the invention used as a PDQ generate weaker acids than produced by a distinct photoacid generator compound present in the same or adjoining composition such as the same photoresist composition. Thus, without being bound by theory, as the strong acid generated by the distinct photoacid generator in an exposed photoresist region migrates to unexposed photoresist areas, the photo-destroyable quencher with higher pKa in the unexposed region quenches the strong acid diffused from exposed region. This can result in neutralization of strong acid in the unexposed region and thereby improve lithographic results.

Thus, in certain preferred aspects, an acidic component of a Te-containing PDQ a resist composition will differ in pKa by 0.5, 1, 2, 3 or 4 or more from the acidic component of a distinct photoacid generator compound present in the same photoresist composition.

Methods are also provided for forming relief images of photoresist compositions of the invention (including patterned lines with sub sub-50 nm or sub-20 nm dimensions). Such methods may comprise, for example: a) applying a coating layer of a photoresist of the invention on a substrate; b) exposing the photoresist composition layer to activating radiation including EUV; and c) developing the exposed photoresist composition coating layer.

Substrates such as a microelectronic wafer also are provided having coated thereon a photoresist composition of the invention. Electronic devices formed by the disclosed methods are also provided, Other aspects of the invention are discussed infra.

DETAILED DESCRIPTION

As referred to herein, acid generator compounds can produce an acid when exposed to activating radiation, such as EUV radiation, e-beam radiation or other radiation sources such as 193 nm wavelength radiation. Acid generator compounds as referred to herein also may be referred to as photoacid generator compounds.

The term Te-salt refers to a salt compound as disclosed herein that comprises one or more Te atoms.

As also discussed, preferred Te-salts may be photoactive and reactive to photolithography radiation such as 193 nm and EUV radiation. Such preferred Te-salts can be used as a photoactive component of a photoresists. However, the invention also includes in other aspects Te-salts that may not be photoactive including with respect to such radiation, or may not be used at least directly or otherwise as a photoactive resist component.

As discussed above, preferred Te-salts include those of Formulae (I), (IIA), (IIB), (III) and (IIIA), as defined above.

In those above Formulae (I), (IIA), (IIB), (III) and (IIIA), suitable non-hydrogen substituents may be e.g. halo (F, Cl, Br or I); cynano, nitro, optionally substituted C1-20alkyl, optionally substituted C1-20alkoxy, such as optionally substituted alkyl (e.g. optionally substituted C1-10 alkyl), optionally substituted alkenyl or alkynyl preferably having 2 to about 20 carbon atoms such as such as allyl; optionally substituted ketones preferably having 1 to about 20 carbon atoms; optionally substituted alkylthio preferably having 1 to about 20 carbon atoms; optionally substituted alkylsulfinyl preferably 1 to about 20 carbon atoms; optionally substituted alkylsulfonyl preferably having 1 to about 20 carbon atoms; optionally substituted carboxy preferably have 1 to about 20 carbon atoms (which includes groups such as —COOR' where R' is H or $C_{1-8}$ alkyl, including esters that are substantially non-reactive with photoacid); optionally substituted alkaryl such as optionally substituted benzyl, optionally substituted carbocyclic aryl such as optionally substituted phenyl, naphthyl, acenaphthyl, or optionally substituted heteroalicyclic or heteroaromatic group such as pyridyl, furanyl, pyrrole, thiophene, furan, imidazole, pyrazole, oxazole, isoxazole, thiazole, isothiazole, triazole, furanzan, oxadiazole, thiadiazole, dithiazole, terazole, pyran, thiopyran, diazine, oxazine, thiazine, dioxine, dithine, and triazine and polyaromatic groups containing one or more of such moieties.

As discussed, Te-salts of the above formulae may be suitably substituted at available positions by one or more acid-labile groups. Suitable acid-labile groups may be a variety of moieties, including acid-labile esters and acetals such as optionally substituted ethylcyclopentyl ester, methyladamantyl ester, ethyl adamantyl ester, t-butylester, phenyl ester, naphthyl ester, ethoxy ethyl ethers and esters and others. In certain preferred aspects, a Te-salt compound of the invention will contain 1 or 2 covalently linked acid-labile groups. As referred to herein, acid-labile moieties or groups (including acid-labile esters and acetals) undergo reaction in the presence of generated acid (from an acid generator compound in a resist which may be a Te-salt present in the resist) during typical lithographic processing, including any post-radiation exposure thermal exposure. Acid-labile groups as referred to herein also may be referred to as photoacid-labile groups.

The present Te-salts compounds can be readily prepared. See, for instance, the syntheses set forth in the examples, which follow.

Specifically preferred compounds of the invention include the following:

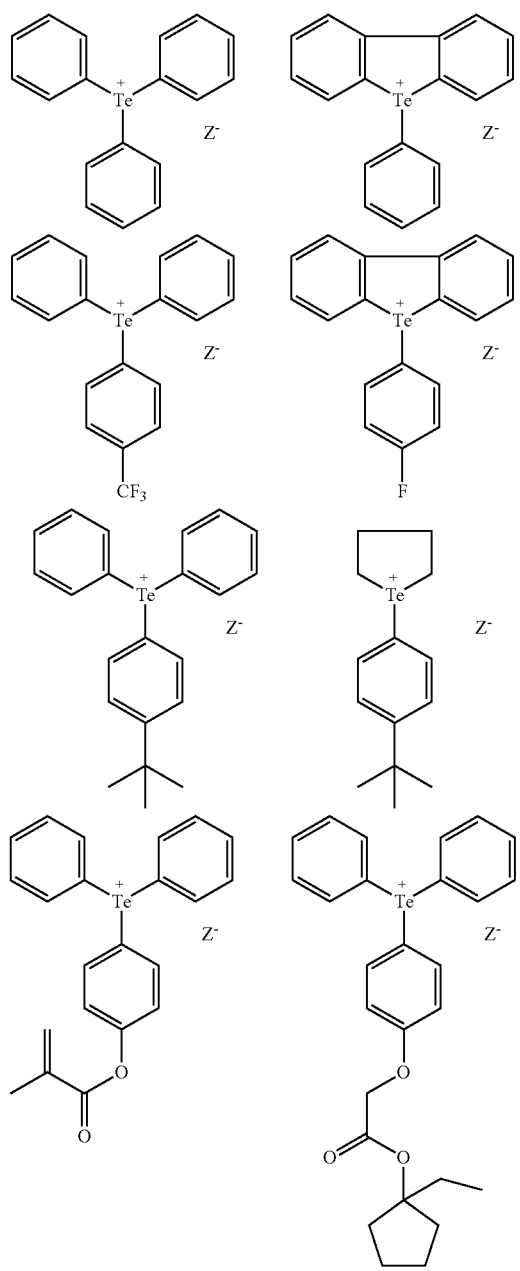

where in the above structures Z is a counter anion as defined for any of the above Formulae (I), (IIA), (IIB), (III) and (IIIA).

Photoresist Compositions

As discussed above, Te-salts as disclosed herein are useful as the radiation sensitive component in photoresist compositions, including both positive-acting and negative-acting chemically amplified resist compositions.

The photoresists of the invention typically comprise a polymer and one or more Te-salts as disclosed herein. Preferably the polymer has functional groups that impart alkaline aqueous developability to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Te-salts of the invention are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-labile monomer having the below formula (V), a lactone-containing monomer of the formula (VI), a base-soluble monomer of formula (VII) for adjusting dissolution rate in alkaline developer, and a photoacid-generating monomer of the formula (VIII), or a combination comprising at least one of the foregoing monomers:

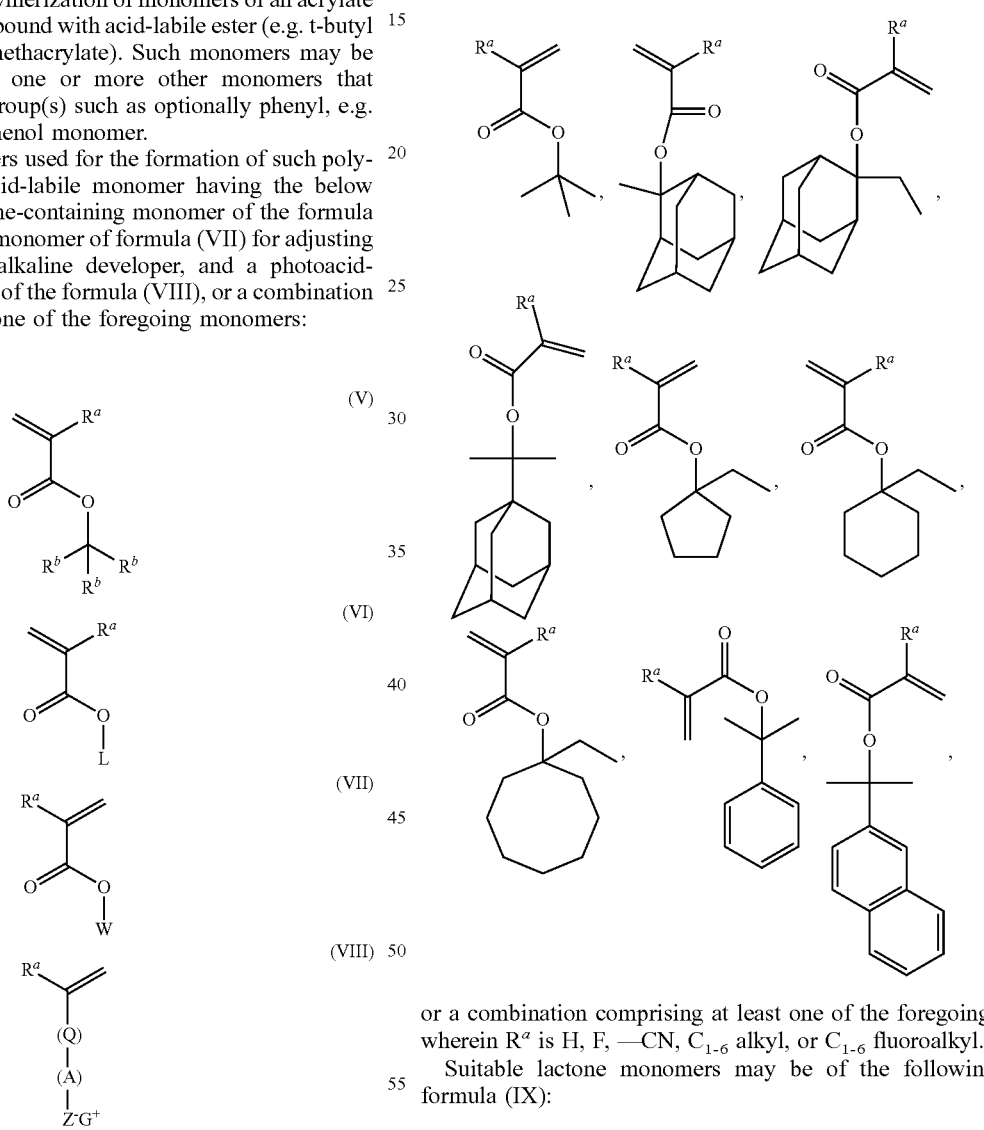

wherein each $R^a$ is independently H, F, —CN, $C_{1\text{-}10}$ alkyl, or $C_{1\text{-}10}$ fluoroalkyl. In the acid-deprotectable monomer of formula (V), $R^b$ is independently $C_{1\text{-}20}$ alkyl, $C_{3\text{-}20}$ cycloalkyl, $C_{6\text{-}20}$ aryl, or $C_{7\text{-}20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4\text{-}20}$ lactone-containing group. In the base solubilizing monomer of formula (VII), W is a halogenated or non-halogenated, aromatic or non-aromatic $C_{2\text{-}50}$ hydroxyl-containing organic group having a pKa of less than or equal to 12. In the photoacid generating monomer of formula (VIII), Q is ester-containing or non-ester containing and fluorinated or non-fluorinated and is $C_{1\text{-}20}$ alkyl, $C_{3\text{-}20}$ cycloalkyl, $C_{6\text{-}20}$ aryl, or $C_{7\text{-}20}$ aralkyl group, A is ester-containing or non-ester-containing and fluorinated or non-fluorinated, and is $C_{1\text{-}20}$ alkyl, $C_{3\text{-}20}$ cycloalkyl, $C_{6\text{-}20}$ aryl, or $C_{7\text{-}20}$ aralkyl, $Z^-$ is an anionic moiety comprising carboxylate, sulfonate, an anion of a sulfonamide, or an anion of a sulfonimide, and $G^+$ is a sulfonium or iodonium cation.

Exemplary acid-labile monomers include but are not limited to:

or a combination comprising at least one of the foregoing, wherein $R^a$ is H, F, —CN, $C_{1\text{-}6}$ alkyl, or $C_{1\text{-}6}$ fluoroalkyl.

Suitable lactone monomers may be of the following formula (IX):

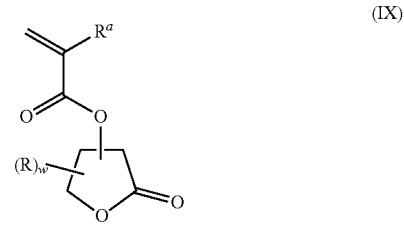

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

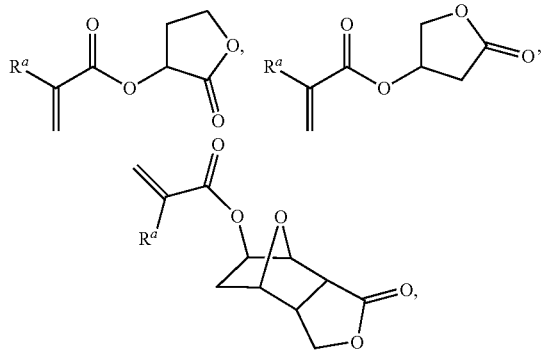

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

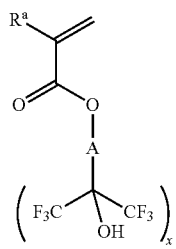

(X)

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

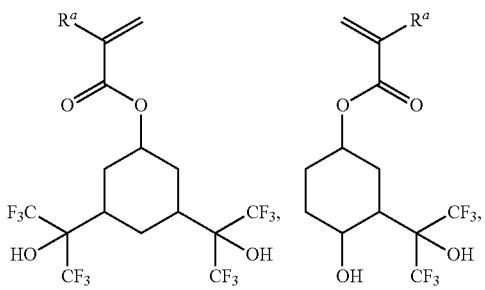

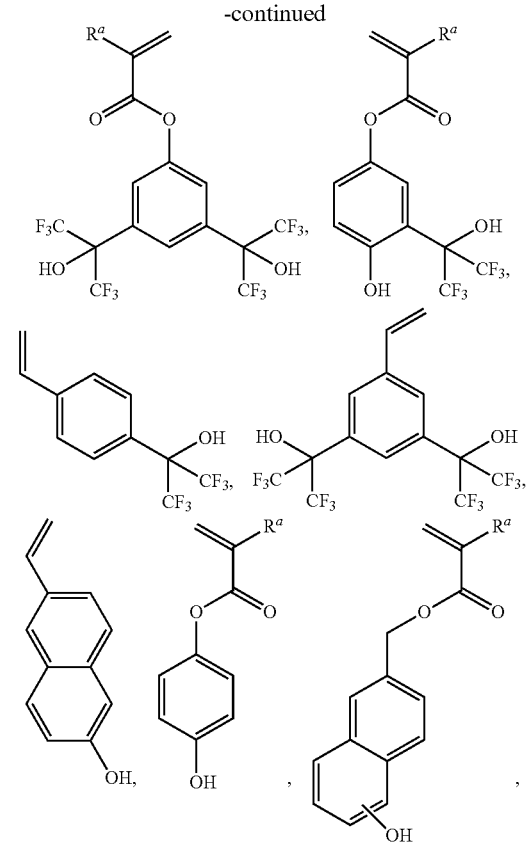

or a combination comprising at least one of the foregoing, wherein $R^a$ is H, F, —CN, $C_{1-6}$ alkyl, or $C_{1-6}$ fluoroalkyl.

Preferred photoacid generating monomer include those of the formulae (XI) or (XII):

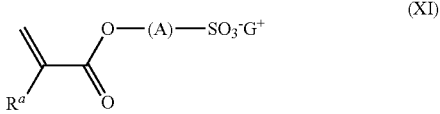

(XI)

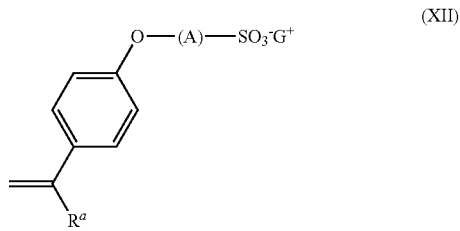

(XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[C(R$^1$)$_2$)$_x$C(=O)O]$_b$—C((R$^2$)$_2$)$_y$(CF$_2$)$_z$— group, or an o-, m- or p-substituted —C$_6$F$_4$— group, where each R$^1$ and R$^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred photoacid generating monomers include:

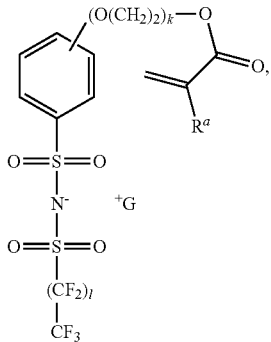

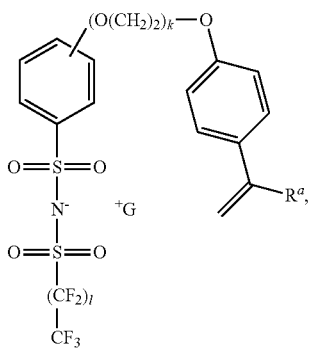

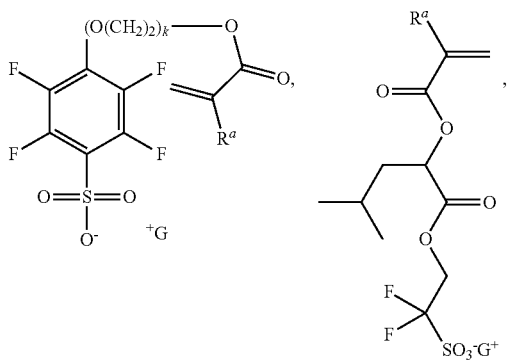

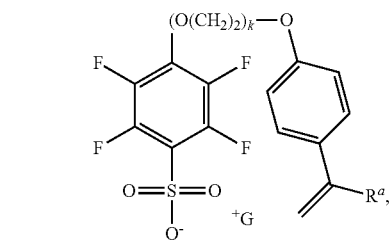

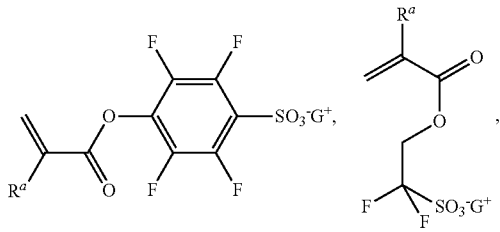

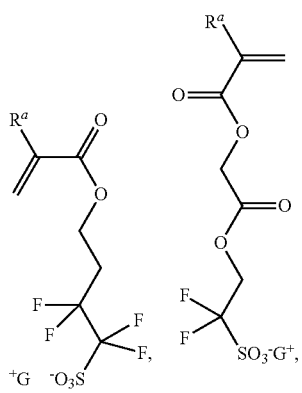

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation.

Preferred photoacid-generating monomers may include sulfonium or iodonium cation. Preferably, in formula (IV), $G^+$ is of the formula (XIII):

(XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

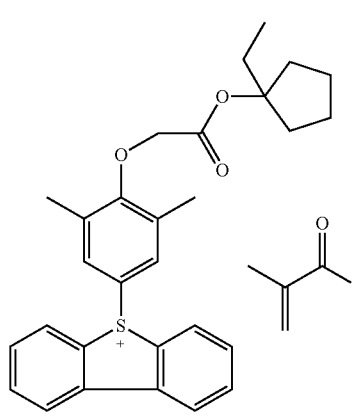

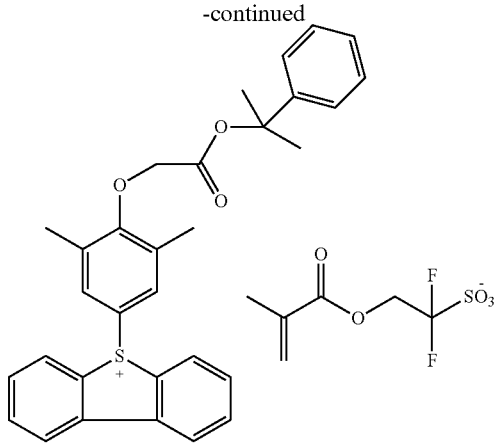

wherein $R^a$ is H, F, —CN, $C_{1-6}$ alkyl, or $C_{1-6}$ fluoroalkyl.

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Polymers for use in photoresists of the invention may suitably vary widely in molecular weight and polydispersity. Suitable polymers include those that have a $M_w$ of from about 1,000 to about 50,000, more typically about 2,000 to about 30,000 with a molecular weight distribution of about 3 or less, more typically a molecular weight distribution of about 2 or less.

Photoresists of the invention also may contain other materials. For example, other optional additives include actinic and contrast dyes, anti-striation agents, plasticizers, speed enhancers, sensitizers, photodestroyable bases etc. Such optional additives typically will be present in minor concentration in a photoresist composition.

Inclusion of base materials, preferably the carboxylate or sulfonate salts of photo-decomposable cations, provides a mechanism for neutralization of acid from the acid decomposable groups, and limits the diffusion of the photogenerated acid, to thereby provide improved contrast in the photoresist.

Photo-destroyable bases include photo-decomposable cations, and preferably those also useful for preparing acid generator compounds, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, 1,1',1"-nitrilotripropan-2-ol, 1,1',1",1'"-(ethane-1,2-diylbis(azanetriyl))tetrapropan-2-ol; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the copolymer in an amount of 50 to 99 wt %, specifically 55 to 95 wt %, more specifically 60 to 90 wt %, and still more specifically 65 to 90 based on the total weight of solids. The photo-destroyable base if utilized may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generator compound(s) should be present in an amount sufficient to enable generation of a latent image in a coating layer of the resist. More specifically, the one or more acid generator compounds will suitably be present in an amount of from about 1 to 50 weight percent of total solids of a resist. It will be understood that the solids includes copolymer, photo-destroyable base, quencher, surfactant, any added PAG, and any optional additives, exclusive of solvent.

A coated substrate may be formed from the photoresist containing acid generator compound(s) (which may be one or more Te-salts as disclosed herein) which should be present in an amount sufficient to enable generation of a latent image in a coating layer of the resist and acid generator compound. Such a coated substrate includes: (a) a substrate having one or more layers to be patterned on a surface thereof; and (b) a layer of the photoresist composition including the acid generator compound over the one or more layers to be patterned. For EUV or e beam imaging, photoresists may suitably have relatively higher content of acid generator compound(s), e.g. where the one or more acid generator compounds comprise 5 to 10 to about 65 weight percent of total solids of the resist. Typically, lesser amounts of the photoactive component will be suitable for chemically amplified resists.

The photoresists of the invention are generally prepared following known procedures with the exception that one or more Te-salts of the invention are included in the photoresist and in certain aspects are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and terahydrofuran.

The photoresist may, when used in one or more such a pattern-forming processes, be used to fabricate electronic and optoelectronic devices such as memory devices, processor chips (CPU's), graphics chips, and other such devices.

The following examples are illustrative of the invention.

Examples 1-4: Te-Salt Syntheses

Example 1

The synthetic scheme for the Te-salt (photoacid generator) designated TPTe AdOH-TFPS is shown in Scheme 1 immediately below. The synthesis of the salt TPTe Cl (1) is described by W. H. H. Gunther in Journal of Organometallic Chemistry, 1974, 74, 79-84. The synthesis of the salt AdOH-TFPS Na (2) is described in U.S. Pat. No. 934,822B2 of Aqad et al. A solution made of salt 1 (10.0 g, 25.35 mmol) and salt 2 (11 g, 25.80 mmol) in a mixture of 75 mL dichloromethane and 75 mL water is stirred at room temperature. The organic phase is separated, washed five times with 50 mL of deionized water, concentrated, and poured into heptane to obtain the Te-salt (photoacid generator compound) TPTe AdOH-TFPS

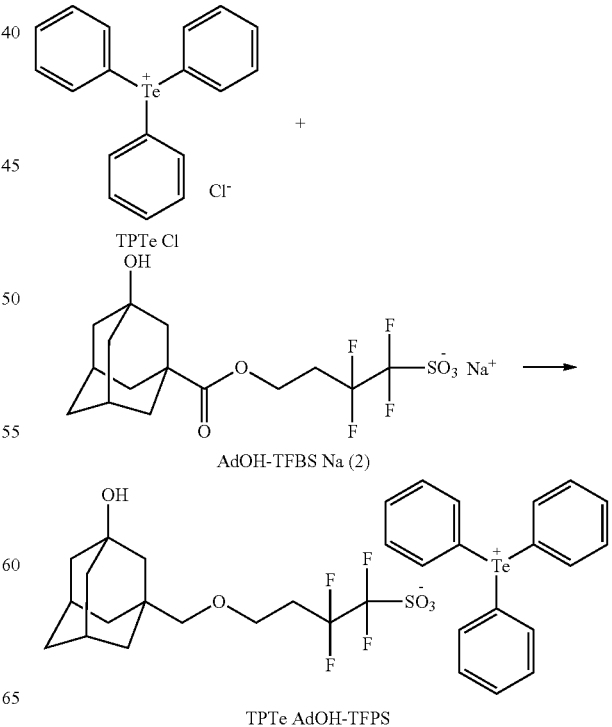

Scheme 1

Example 2

The synthetic scheme for the Te-salt (photoacid generator) designated PDBTe AdOH-TFPS is shown in Scheme 2 immediately below. The synthesis of the salt PDBTe BF₄ (3) is described by Sato et al in Tetrahedron Letters, 36(16), 2803-6; 1995. A solution made of salt 3 (5.0 g, 11.72 mmol) and salt (2) (5.0 g, 5.70 mmol) in a mixture of 75 mL dichloromethane and 75 mL water is stirred at room temperature for 16 hours. The organic phase is separated, washed five times with 50 mL of deionized water, concentrated, and poured into heptane to obtain the Te-salt (photoacid generator compound) PDBTe AdOH-TFPS.

Scheme 2

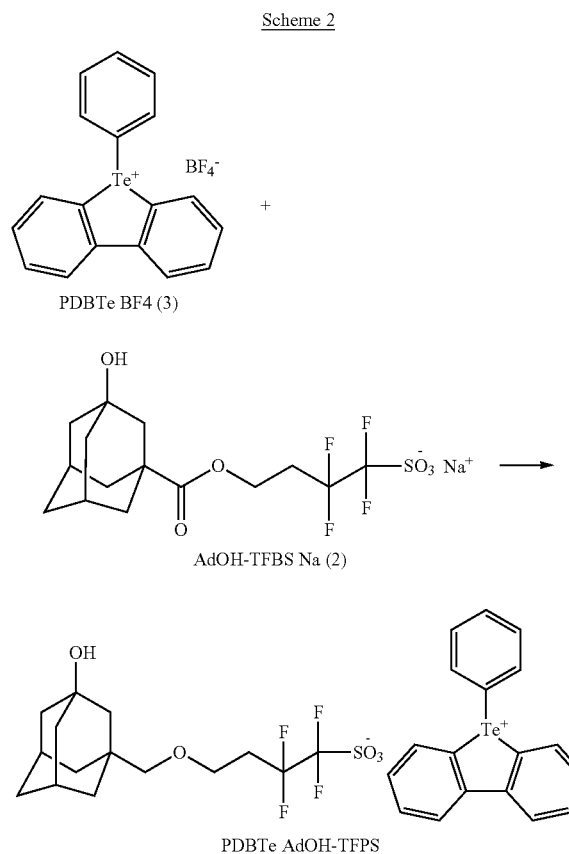

Example 3

The synthetic scheme for the Te-salt (photoactive compound) designated TPTe CS is shown in Scheme 3 immediately below. The synthesis of Camphorsulfonate Silver Salt (CSAg) is described in U.S. Patent US20140186767A1 of Thackeray et al. A solution made of TPTe Cl (10.0 g, 25.35 mmol) and salt CSAg (8.6 g, 25.35 mmol) in a mixture of 50 mL methanol is stirred at room temperature overnight. The reaction mixture is filtered and concentrated to obtain the Te-salt (photoacid generator compound) TPTe CS.

Scheme 3

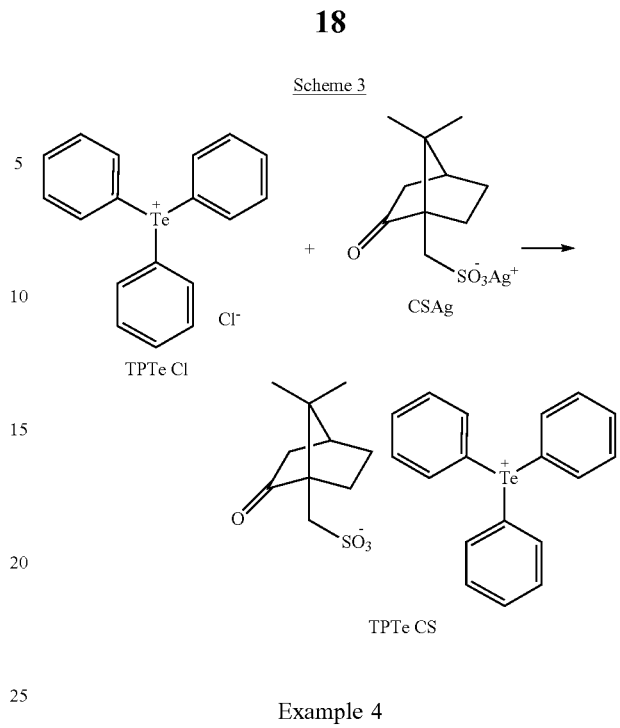

Example 4

The synthetic scheme for the Te-salt (photoactive compound) designated TPTe HAdC is shown in Scheme 4 immediately below. The synthesis of 3-hydroxyadamantanecarboxylic acid silver salt (HAdCAg) is described in U.S. Patent US20140186767A1 of Thackeray et al. A solution made of TPTe Cl (10.0 g, 25.35 mmol) and salt HAdCAg (7.68 g, 25.35 mmol) in a mixture of 50 mL methanol is stirred at room temperature overnight. The reaction mixture is filtered and concentrated to obtain the Te-salt (photoacid generator compound) TPTe HAdC.

Scheme 4

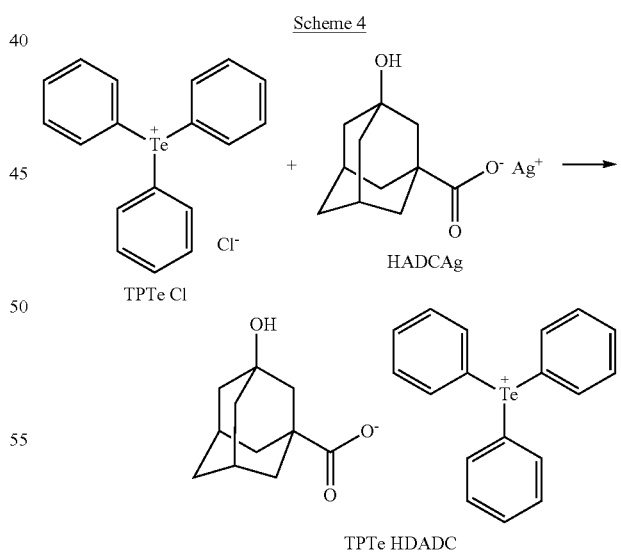

Examples 5-7: EUV Transmission Calculations

The effect of using new Telluronium salts on film absorption at EUV radiation is exemplified by the transmission calculation results. The transmissions at EUV exposure (13.5 nm) for films made from composition examples were calculated from the Center for X-Ray Optics at Lawrence Berkeley National Laboratory web site by inputting the calculated composition molecular formula and assuming a polymer density of 1.20 g/cm³ and film thickness of 60 nm.

Example 5

Table 1 shows the calculated % transmission of compositions that comprise the base polymer P1 (shown in Scheme 5) and Te-salt (photoacid generator). Comparative compositions C1 to C4 comprise polymer P1 and the photoacid generator triphenylsulfionium triftlate (TPS Tf) at 5 mole %, 10 mole %, 15 mol % or 20 mol % respectively. The inventive compositions I1 to I4 comprise polymer P1 and the photoacid generator triphenyltelluronium triftlate (TPTe Tf) at 5 mole %, 10 mole %, 15 mol % or 20 mol % respectively. As can be seen from Table 1, less transmission is obtained for formulations that comprise the inventive TPTe Tf. Interestingly, formulation I1 that comprise TPTe Tf at 5 mol % has less transmission than formulation C4 which comprise TPS Tf at 20 mole %.

Scheme 5

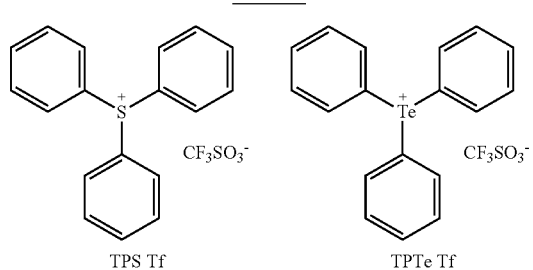

TPS Tf  TPTe Tf

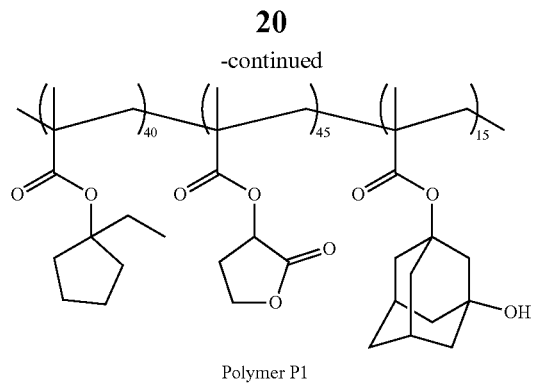

Polymer P1

TABLE 1

| Composition | Polymer | PAG | PAG mol % in composition | 13.5 nm % Transmittance at FT = 60 nm |
|---|---|---|---|---|
| C1 (comparative) | P1 | TPS Tf | 5 | 74.63 |
| C2 (comparative) | P1 | TPS Tf | 10 | 74.13 |
| C3 (comparative) | P1 | TPS Tf | 15 | 74.27 |
| C4 (comparative) | P | TPS Tf | 20 | 74.19 |
| I1 | P1 | TPTe Tf | 5 | 73.14 |
| I2 | P1 | TPTe Tf | 10 | 71.95 |
| I3 | P1 | TPTe Tf | 15 | 70.95 |
| I4 | P1 | TPTe Tf | 20 | 70.09 |

Example 6

Table 2 below shows the calculated % transmission of compositions that comprise polymer-bound PAG (PBP). Comparative composition C5 comprise polymer PBP1 wherein the photoactive cation is triphenylsulfonium and the inventive composition I5 comprise polymer PBP2 wherein the photoactive cation is triphenyltelluronium (FIG. 6). As can be seen from Table 2, less transmission is obtained for formulations that comprise the inventive PBP2.

Scheme 6

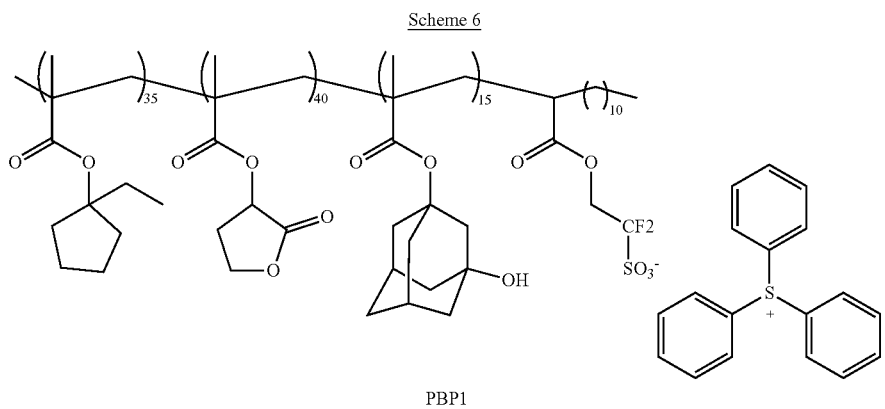

PBP1

-continued

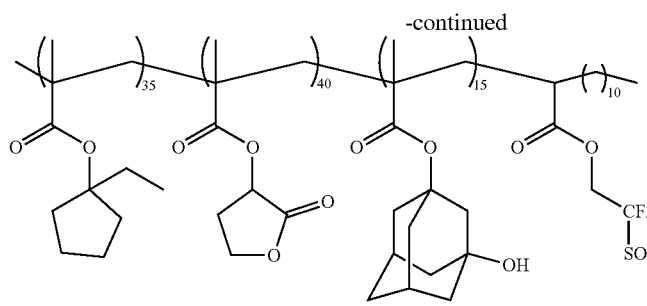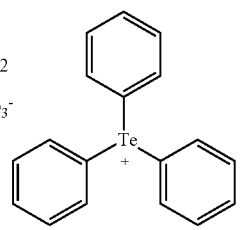

PBP2

TABLE 2

| Composition | Polymer | 13.5 nm % Transmittance at FT = 60 nm |
|---|---|---|
| C5 (comparative) | PBP1 | 74.61 |
| I5 | PBP2 | 72.10 |

Example 7

Table 3 below shows the calculated % transmission of compositions that comprise polymer-bound PAG (PBP). Comparative composition C6 comprises polymer PBP3 wherein the triphenylsulfonium cation is bound to the polymer main chain and the inventive composition 16 comprise polymer PBP4 triphenyltelluronium cation is bound to the polymer main chain (Scheme 7). As can be seen from Table 4 below, less transmission is obtained for formulations that comprise the inventive PBP4.

Scheme 7

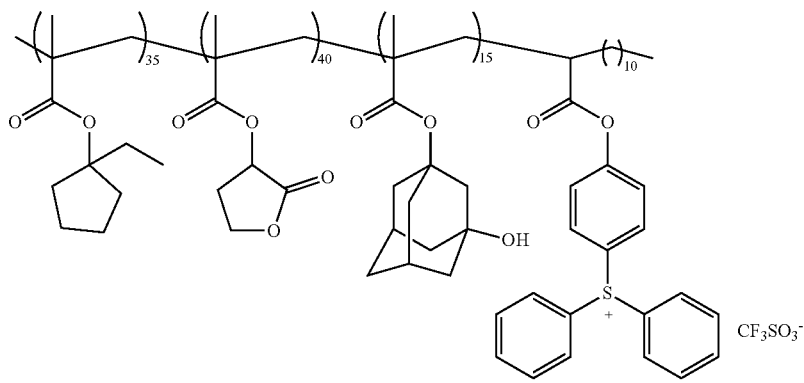

PBP3

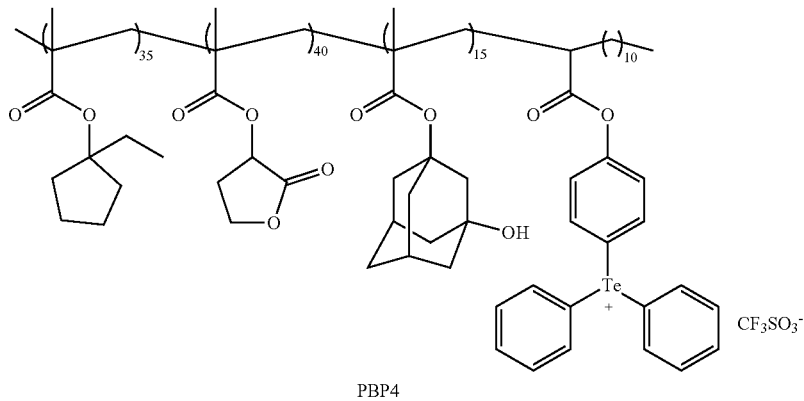

PBP4

TABLE 3

| Composition | Polymer | 13.5 nm % Transmittance at FT = 60 nm |
|---|---|---|
| C6 (comparative) | PBP3 | 74.20 |
| I6 | PBP4 | 71.75 |

What is claimed is:

1. A photoresist composition, comprising:

a resin; and one or more salts of Formula (I):

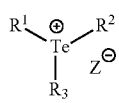

(I)

wherein, $R^1$, $R^2$, and $R^3$ are each independently a $C_{6-60}$ aryl group, a $C_{6-20}$ fluoroaryl group, a $C_{1-20}$ heteroaryl group, a non-fluorinated $C_{1-20}$ alkyl group, a non-fluorinated $C_{3-20}$ cycloalkyl group, a $C_{2-20}$ alkenyl group, or a $C_{2-20}$ fluoroalkenyl group, each of which is substituted or unsubstituted, wherein each $R^1$ is either separate or connected to $R^2$ and/or $R^3$ to form a ring, Z comprises a counter anion comprising an inorganic group selected from $SbF_6^-$, $BF_4^-$, or $B(C_6F_5)_4^-$, a carboxylate, or an anion of a sulfonamide, and wherein the one or more salts comprises one or more acid-labile groups.

2. The photoresist composition of claim 1, wherein the one or more salts correspond to Formula (IIA):

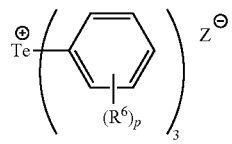

(IIA)

wherein, $R^4$ and $R^5$ are each independently a $C_{6-60}$ aryl group, a $C_{6-20}$ fluoroaryl group, a $C_{1-20}$ heteroaryl group, a $C_{2-20}$ heteroaralkyl group, a $C_{2-20}$ fluoroheteroaralkyl group, a non-fluorinated $C_{1-20}$ alkyl group, a non-fluorinated $C_{3-20}$ cycloalkyl group, a $C_{2-20}$ alkenyl group, or a $C_{2-20}$ fluoroalkenyl group, each of which is substituted or unsubstituted;

each $R^6$ is the same or different non-hydrogen substituent;

p is an integer of 0 to 5; and

Z comprises the counter anion.

3. The photoresist composition of claim 1, wherein the one or more salts correspond to Formula (IIB):

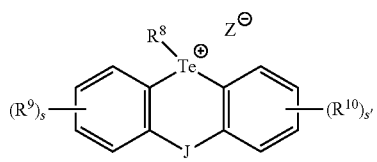

(IIB)

wherein, each $R^6$ is independently a halogen, —CN, —OH, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, or a $C_{3-10}$ fluorocycloalkoxy group, each of which except a halogen, —CN, and —OH may be substituted or unsubstituted;

each p is the same or different integer of 0 to 5; and

Z comprises the counter anion.

4. The photoresist composition of claim 1, wherein the one or more salts correspond to Formula (IIIA):

(IIIA)

wherein:

$R^8$ is a $C_{6-60}$ aryl group, a $C_{6-20}$ fluoroaryl group, a $C_{1-20}$ heteroaryl group, a non-fluorinated $C_{1-20}$ alkyl group, a non-fluorinated $C_{3-20}$ cycloalkyl group, a $C_{2-20}$ alkenyl group, or a $C_{2-20}$ fluoroalkenyl group, each of which is substituted or unsubstituted;

$R^9$ and $R^{10}$ are the same or different non-hydrogen substituents;

J a single bond or a connecting group that may be selected from S, O, C=O, S=O, $SO_2$, or O—C=O;

s and s' are each independently an integer of 0, 1, 2, 3, and 4; and

Z comprises the counter anion.

5. The photoresist composition of claim 1, wherein the photoresist composition comprises one or more acid generator compounds that are distinct from the one or more salts.

6. The photoresist composition of claim 1, wherein the one or more salts are selected from one or more of the following:

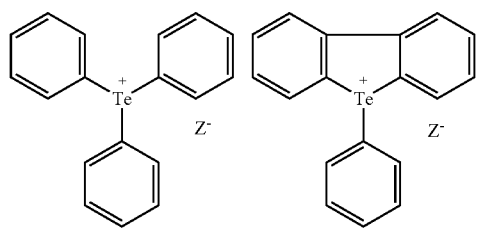

-continued

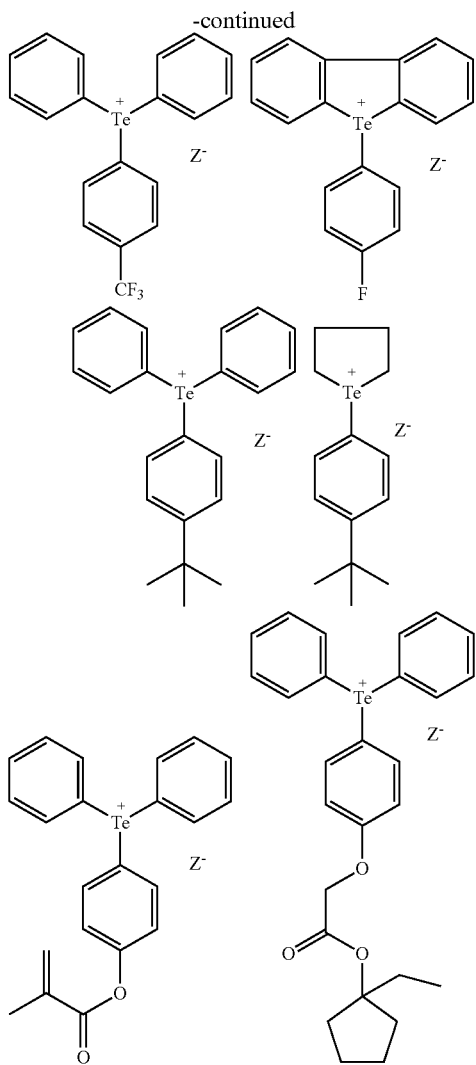

wherein Z is the counter anion.

7. A photoresist composition, comprising:
a resin; and
one or more salts of Formula (III):

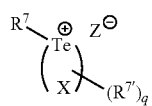

wherein,
X is a single bond or a connecting group that is S, O, C=O, S=O, SO$_2$, O—C=O, carbon, or nitrogen, or oxygen that together with the depicted Te atom forms a single ring group or a multiple fused or linked ring structure;
R$^7$ is a C$_{6-60}$ aryl group, a C$_{6-20}$ fluoroaryl group, a C$_{1-20}$ heteroaryl group, a non-fluorinated C$_{1-20}$ alkyl group, a non-fluorinated C$_{3-20}$ cycloalkyl group, a C$_{2-20}$ alkenyl group, or a C$_{2-20}$ fluoroalkenyl group, each of which is substituted or unsubstituted;
each R$^{7'}$ is the same or different non-hydrogen ring substituent;

q is an integer equal to 0 to the maximum valance permitted by the ring members; and
Z comprises a counter anion comprising an inorganic group selected from SbF$_6^-$, BF$_4^-$, or B(C$_6$F$_5$)$_4^x$, a carboxylate, or an anion of a sulfonamide,
wherein the one or more salts comprises one or more acid-labile groups.

8. A method for providing a photoresist relief image, the method comprising:
a) applying a coating layer of a photoresist composition of claim 1 on a substrate; and
b) exposing the photoresist composition layer to activating radiation and developing the exposed photoresist composition coating layer.

9. The method of claim 8, wherein the one or more salts correspond to Formula (IIA):

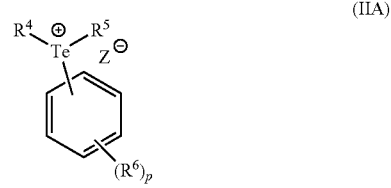

wherein,
R$^4$ and R$^5$ are each independently a C$_{6-60}$ aryl group, a C$_{6-20}$ fluoroaryl group, a C$_{1-20}$ heteroaryl group, a non-fluorinated C$_{1-20}$ alkyl group, a non-fluorinated C$_{3-20}$ cycloalkyl group, a C$_{2-20}$ alkenyl group, or a C$_{2-20}$ fluoroalkenyl group, each of which is substituted or unsubstituted;
each R$^6$ is the same or different non-hydrogen substituent;
p is an integer of 0 to 5; and
Z comprises the counter anion.

10. The method of claim 8, wherein the one or more salts correspond to Formula (IIB):

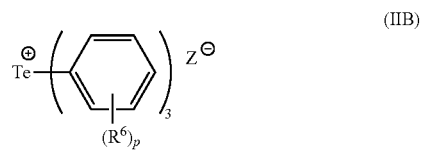

wherein,
each R$^6$ is independently a halogen, —CN, —OH, a C$_{1-10}$ alkyl group, a C$_{1-10}$ fluoroalkyl group, a C$_{1-10}$ alkoxy group, a C$_{1-10}$ fluoroalkoxy group, a C$_{3-10}$ cycloalkyl group, a C$_{3-10}$ fluorocycloalkyl group, a C$_{3-10}$ cycloalkoxy group, or a C$_{3-10}$ fluorocycloalkoxy group, each of which except a halogen, —CN, and —OH may be substituted or unsubstituted;
each p is the same or different integer of 0 to 5; and
Z comprises the counter anion.

11. The method of claim 8, wherein the one or more salts correspond to Formula (IIIA):

(IIIA)

[Structure: Dibenzo-tellurophene type cation with R⁸ on Te⁺, (R⁹)ₛ and (R¹⁰)ₛ' substituents on the two benzene rings, J connecting group, Z⁻ counter anion]

wherein:

R⁸ is a $C_{6-60}$ aryl group, a $C_{6-20}$ fluoroaryl group, a $C_{1-20}$ heteroaryl group, a non-fluorinated $C_{1-20}$ alkyl group, a non-fluorinated $C_{3-20}$ cycloalkyl group, a $C_{2-20}$ alkenyl group, or a $C_{2-20}$ fluoroalkenyl group, each of which is substituted or unsubstituted;

R⁹ and R¹⁰ are the same or different non-hydrogen substituents;

J a single bond or a connecting group that may be selected from S, O, C=O, S=O, SO₂, or O—C=O;

s and s' are each independently an integer of 0, 1, 2, 3, and 4; and

Z comprises the counter anion.

12. The method of claim 8, wherein the one or more salts are selected from one or more of the following:

[Structures of various telluronium salts with Z⁻ counter anions]

wherein Z is the counter anion.

13. The method of claim 8, wherein the photoresist composition layer is exposed to 193 nm radiation.

14. The method of claim 8, wherein the photoresist composition layer is exposed to EUV radiation.

15. A method for providing a photoresist relief image, the method comprising:
  a) applying a coating layer of a photoresist composition of claim 7 on a substrate; and
  b) exposing the photoresist composition layer to activating radiation and developing the exposed photoresist composition coating layer.

16. The method of claim 15, wherein the one or more salts are selected from one or more of the following:

[Structures of various telluronium salts with Z⁻ counter anions]

wherein Z is the counter anion.

17. The photoresist composition of claim 1, wherein the composition further comprises a photodecomposable quencher having an anion of an acid having a pKa>2.

* * * * *